(12) United States Patent
Watanabe et al.

(10) Patent No.: US 7,012,161 B2
(45) Date of Patent: Mar. 14, 2006

(54) COMPOUND, FLUORINE-CONTAINING POLYMERIZABLE CYCLIC OLEFIN COMPOUND

(75) Inventors: Takeru Watanabe, Niigata (JP); Takeshi Kinsho, Niigata (JP); Yuji Harada, Niigata (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 18 days.

(21) Appl. No.: 10/918,465

(22) Filed: Aug. 16, 2004

(65) Prior Publication Data

US 2005/0054883 A1   Mar. 10, 2005

(30) Foreign Application Priority Data

Sep. 10, 2003 (JP) .............................. 2003-318803

(51) Int. Cl.
C07C 49/21 (2006.01)
C07C 49/215 (2006.01)
C07C 45/63 (2006.01)
C08F 114/18 (2006.01)
G03C 1/492 (2006.01)

(52) U.S. Cl. ............... 568/368; 568/343; 568/347; 568/817; 568/823; 526/242; 526/244; 430/270.1

(58) Field of Classification Search ............... 568/368, 568/343, 347, 817, 823
See application file for complete search history.

(56) References Cited

U.S. PATENT DOCUMENTS 6,124,074 A * 9/2000 Varanasi et al. ......... 430/270.1
6,800,418 B1 * 10/2004 Yoon et al. ............. 430/270.1

FOREIGN PATENT DOCUMENTS

JP   A 2001-328964   11/2001
JP   A 2002-255875    9/2002

* cited by examiner

Primary Examiner—Sikarl A. Witherspoon
(74) Attorney, Agent, or Firm—Oliff & Berridge, PLC

(57) ABSTRACT

There is disclosed a fluorine-containing polymerizable cyclic olefin compound that has one or more partial structures represented by the following general formula (1) or (2). There can be provided a novel fluorine-containing polymerizable cyclic olefin compound which is excellent in transparency to irradiation, for example, at a wavelength of 200 nm or less, especially at a wavelength of 160 nm or less and dry etching resistance, has low hydrophobicity, and is excellent in development characteristics, and thus is useful as a raw material for a base resin of photoresist composition

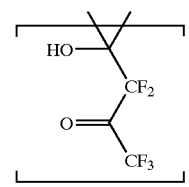

(1)

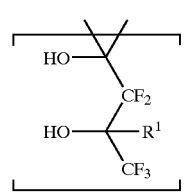

(2)

5 Claims, No Drawings

COMPOUND, FLUORINE-CONTAINING POLYMERIZABLE CYCLIC OLEFIN COMPOUND

BACKGROUND OF INVENTION

1. Field of the Invention

The present invention relates to a novel fluorine-containing polymerizable cyclic olefin compound. Especially, it relates to a fluorine-containing polymerizable cyclic olefin compound which is useful as a raw material for polymers, functional materials, pharmaceutical and agricultural chemicals or the like.

2. Description of the Related Art

A compound wherein fluorine atoms and oxygen functional groups are introduced into a polymerizable cyclic olefin compound, such as norbornene, tetracyclododecene or the like, is used as a monomer, for example, for production of a functional polymer compound, or a raw material for it.

Recently, for using as a base resin of a chemically amplified photoresist composition, it has been tried to synthesize a polymer which has both a high transparency at a wavelength of 200 nm or less, especially at a wavelength of 160 nm or less and an etch resistance, by introducing fluorine atoms and oxygen functional groups into a side chain of a norbornane ring as a main chain, and there have been proposed some monomers used as a raw material for it (see, for example, Japanese patent Laid-Open (kokai) No. 2001-328964 and Japanese patent Laid-Open (kokai) No. 2002-255875). However, introduction of a fluorine atom causes a disadvantage that hydrophobicity of a polymer is increased too much, development characteristics and a resolution are degraded. Therefore, there has been needed a monomer used as a raw material of a still more efficient polymer with low hydrophobicity even if a fluorine atom is introduced.

The present invention has been made in order to solve such problems. The object of the present invention is to provide a novel fluorine-containing polymerizable cyclic olefin compound which is useful as a raw material for polymers, functional materials, pharmaceutical and agricultural chemicals or the like, is excellent in transparency to irradiation, for example, at a wavelength of 200 nm or less, especially at a wavelength of 160 nm or less and in dry etching resistance, has low hydrophobicity, and is excellent in development characteristics, and thus is useful as a base resin of photoresist composition.

DISCLOSURE OF THE INVENTION

To achieve the above mentioned object, the present invention provides a fluorine-containing polymerizable cyclic olefin compound wherein it has one or more partial structures represented by the following general formula (1) or (2).

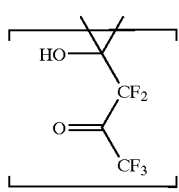
(1)

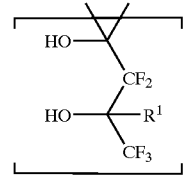
(2)

(In the formulae, $R^1$ represents a hydrogen atom, or a linear, branched or cyclic alkyl group, alkoxy group, acyloxy group, alkylthio group, acyl amino group, and alkyl sulfonyl amino group having 1–15 carbon atoms wherein some or all of hydrogen atoms may be substituted with a halogen atom.)

The polymer which has as a repeating unit the fluorine-containing polymerizable cyclic olefin compound having one or more partial structures represented by the above-mentioned general formula (1) or (2), has a high transparency to irradiation at a wavelength of 200 nm or less, especially at a wavelength of 160 nm or less and a high etch resistance, and furthermore has low hydrophobicity although it contains a fluorine atom. Furthermore, in the fluorine-containing polymerizable cyclic olefin compound represented by the above-mentioned general formula (2), for example, hydrophobicity and hydrophilicity can be controlled optimally depending on a purpose by selecting an optimal group as $R^1$.

It is desirable that the above-mentioned compound is a fluorine-containing polymerizable cyclic olefin compound represented by either of the following general formulae (3), (4), (5) and (6).

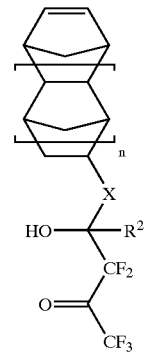
(3)

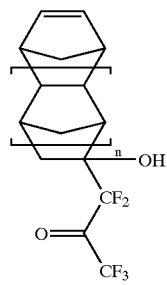
(4)

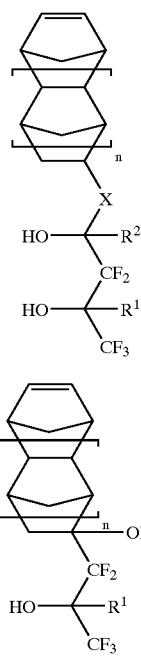

(5)

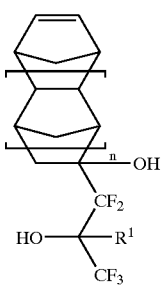

(6)

(In the formulae, $R^1$ represents a hydrogen atom or a linear, branched, or cyclic alkyl group, alkoxy group, acyloxy group, alkylthio group, acyl amino group or alkyl sulfonyl amino group having 1–15 carbon atoms in which some or all of hydrogen atoms may be substituted with a halogen atom, and $R^2$ represents a hydrogen atom or a linear, branched, or cyclic alkyl group having 1–10 carbon atoms in which some or all of hydrogen atoms may be substituted with a halogen atom, and X represents a single bond or a linear, branched, or cyclic alkylene group having 1–10 carbon atoms in which some or all of hydrogen atoms may be substituted with a halogen atom, and n is 0 or 1.)

The polymer derived from the fluorine-containing polymerizable cyclic olefin compound shown by either of the above-mentioned general formulae (3), (4), (5) and (6) as a raw material has an especially high dry etching resistance, and has an especially high transparency to irradiation at a wavelength of 160 nm or less, and has sufficiently low hydrophobicity. Furthermore, performance of the fluorine-containing polymerizable cyclic olefin compounds of the above-mentioned general formulae (3), (5) and (6) can be controlled depending on a purpose by selecting optimal groups as $R^1$ and $R^2$.

Furthermore, the present invention provides a photoresist composition wherein it comprises at least the above-mentioned polymer of the present invention as a base resin.

As described above, the polymer which comprises the fluorine-containing polymerizable cyclic olefin compound of the present invention as a repeating unit has an especially high transparency to irradiation at a wavelength of 160 nm or less, and a high dry etching resistance, and further has low hydrophobicity and a good development characteristics. Therefore, the photoresist composition wherein it is used as a base resin shows a very good resolution, and is used suitably especially as a micropatterning material for the VLSI manufacture.

Furthermore, the present invention provides a manufacturing method of a fluorine-containing polymerizable cyclic olefin compound represented by the following general formula (3) or (4) wherein a cyclic olefin compound containing an aldehyde or a ketone represented by the following general formula (7) or (8) is reacted with metal 1,1,3,3,3-pentafluoro-2-propenyloxide compound.

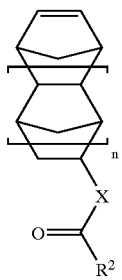

(7)

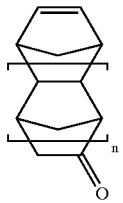

(8)

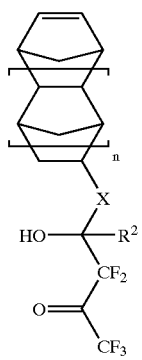

(3)

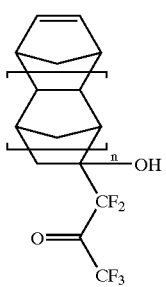

(4)

(In the formulae, $R^2$ represents a hydrogen atom or a linear, branched, or cyclic alkyl group having 1–10 carbon atoms in which some or all of hydrogen atoms may be substituted with a halogen atom, and X represents a single bond or a linear, branched, or cyclic alkylene group having 1–10 carbon atoms in which some or all of hydrogen atoms may be substituted with a halogen atom, and n is 0 or 1.)

Furthermore, the present invention provides a manufacturing method of a fluorine-containing polymerizable cyclic olefin compound represented by the following general formula (5) or (6) wherein a fluorine-containing polymerizable cyclic olefin compound represented by the following general formula (3) or (4) is reacted with a compound $R^1$-Z.

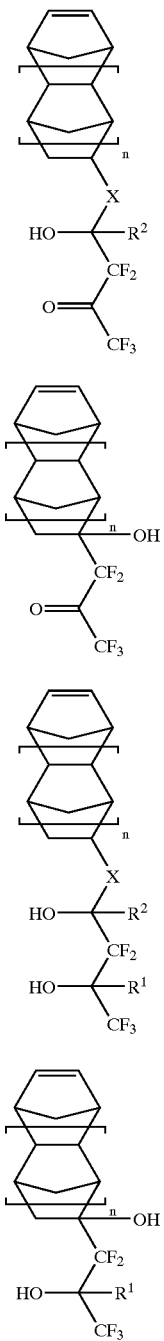

(3)

(4)

(5)

(6)

(In the formulae, $R^1$ represents a hydrogen atom, or a linear, branched or cyclic alkyl group, alkoxy group, acyloxy group, alkylthio group, acyl amino group and alkyl sulfonyl amino group having 1–15 carbon atoms wherein some or all of hydrogen atoms may be substituted with a halogen atom, $R^2$ represents a hydrogen atom or a linear, branched, or cyclic alkyl group having 1–10 carbon atoms in which some or all of hydrogen atoms may be substituted with a halogen atom, and x represents a single bond or a linear, branched, or cyclic alkylene group having 1–10 carbon atoms in which some or all of hydrogen atoms may be substituted with a halogen atom, Z represents a monovalent group such that $R^1$-Z is $R^1$ anion equivalent and n is 0 or 1.)

The novel fluorine-containing polymerizable cyclic olefin compound of the present invention can be easily manufactured in high yield, for example, according to the above-mentioned manufacturing method.

As described above, according to the present invention, there can be provided a novel fluorine-containing polymerizable cyclic olefin compound which is useful as a raw material for polymers, functional materials, pharmaceutical and agricultural chemicals or the like. Among them, the polymer comprising the compound as a repeating unit has an excellent transparency to irradiation at a wavelength of 200 nm or less, especially at a wavelength of 160 nm or less, for example, to $F_2$ laser light, and an excellent dry etching resistance, and has low hydrophobicity and thereby has an excellent development characteristics. Accordingly, it is very useful as a base resin of a photoresist composition.

DESCRIPTION OF THE INVENTION AND EMBODIMENT

Hereafter, the present invention will be explained, but the present invention is not limited thereto.

Inventors have studied an unknown fluorine-containing polymerizable cyclic olefin compound which is to be used as a raw material for the polymer having low hydrophobicity and good development characteristics in addition to high transparency and high etch resistance. As a result, they have found that a fluorine-containing polymerizable cyclic olefin compound which has a partial structure represented by the general formula (1) or (2) can be easily obtained in high yield, and that if the polymer obtained by polymerization of the fluorine-containing polymerizable cyclic olefin compound is used as a base resin, the photoresist composition which is excellent in transparency at a wavelength of 160 nm or less and in dry etching resistance, and is excellent in development characteristics can be obtained, and thereby the present invention has been completed.

That is, the fluorine-containing polymerizable cyclic olefin compound of the present invention has one or more partial structures represented by the following general formula (1) or (2).

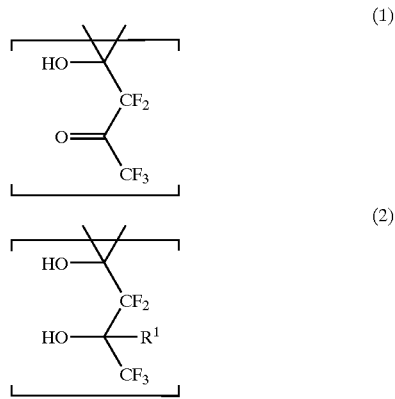

(1)

(2)

(In the formulae, $R^1$ represents a hydrogen atom or a linear, branched, or cyclic alkyl group, alkoxy group, acyloxy group, alkylthio group, acyl amino group or alkyl sulfonyl amino group having 1–15 carbon atoms in which some or all of hydrogen atoms may be substituted with a halogen atom.

It is considered that the fluorinated alkyl part largely contributes to excellent transparency, the alicyclic part largely contributes to high etching resistance, the hydroxyl group and ketone group largely contribute to excellent development characteristics in the structure of the above-mentioned fluorine-containing polymerizable cyclic olefin compound of the present invention. Therefore, the polymer which comprises as a repeating unit such a fluorine-containing polymerizable cyclic olefin compound has high transparency to irradiation at a wavelength of 200 nm or less, especially at a wavelength of 160 nm or less, high etch resistance and low hydrophobicity even though it contains a fluorine atom.

Illustrative examples of the above-mentioned fluorine-containing polymerizable cyclic olefin compound which has one or more partial structures represented by the general formula (1), besides the compound having the structure corresponding to the general formulae (3) and (4), are shown below. However, it is not limited to them.

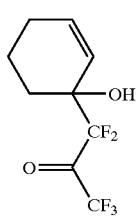
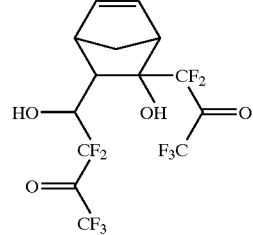

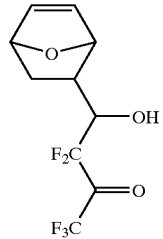

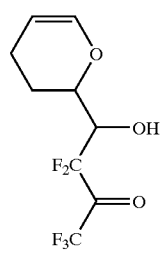

In the above-mentioned general formula (2), $R^1$ represents a hydrogen atom, or a linear, branched or cyclic alkyl group, alkoxy group, acyloxy group, alkylthio group, acyl amino group, and alkyl sulfonyl amino group having 1–15 carbon atoms wherein some or all of hydrogen atoms may be substituted with a halogen atom. Illustrative examples of $R^1$ include: a hydrogen atom, a methyl group, an ethyl group, a propyl group, an isopropyl group, a butyl group, s-butyl group, t-butyl group, a cyclohexyl group, a decyl group, a pentadecyl group, a trichloro methyl group, a trifluoro methyl group, 2,2,2-trifluoro ethyl group, a methoxy group, an ethoxy group, a propoxy group, an isopropoxy group, 2,2,2-trifluoro ethoxy group, 1,1,1,3,3,3-hexafluoro isopropoxy group, a formyloxy group, an acetoxy group, a trifluoro acetoxy group, a methylthio group, an ethylthio group, t-butylthio group, a formylamino group, an acetylamino group, a trifluoro acetyl amino group, N-formyl-N-methyl amino group, a methane sulfonyl amino group, a trifluoromethane sulfonyl amino group, N-methane sulfonyl-N-methyl amino group. However, it is not limited to them.

When the polymer derived from the compound (2) wherein $R^1$ is a hydroxyl group as a raw material is used as a base resin of photoresist composition, developer solubility is unnecessarily high and film loss of a non-exposed area becomes remarkable, and thus it is hard to be used as photoresist. Accordingly, the compound wherein $R^1$ is a hydroxyl group is excluded.

It is possible to control hydrophobicity and hydrophilicity of the compound optimally by choosing $R^1$ depending on a purpose, and thereby to control characteristics of a photoresist in which the compound of the present invention is used. Illustrative examples of fluorine-containing polymerizable cyclic olefin compounds which have one or more partial structures represented by the above-mentioned general formula (2), besides compounds having a structure corresponding to the general formulae (5) and (6), are shown below. However, it is not limited to them.

In the following formulae, Me represents a methyl group, and Ac represents an acetyl group, respectively (hereinafter they represent the same meaning).

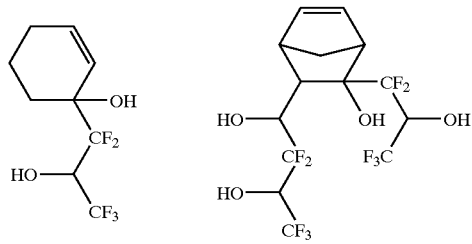

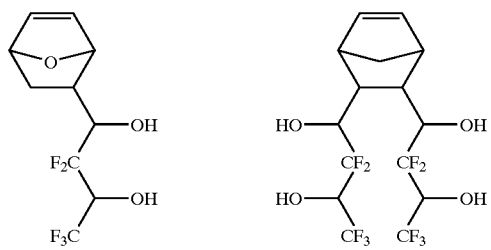

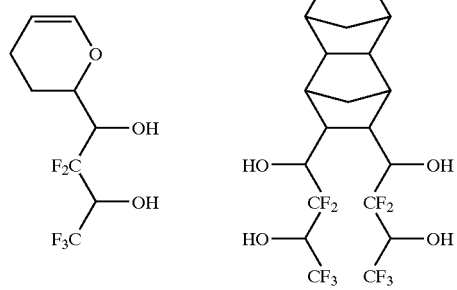

-continued

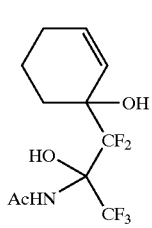
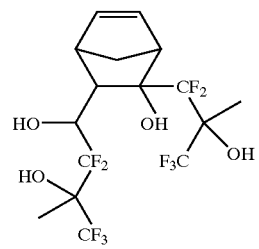
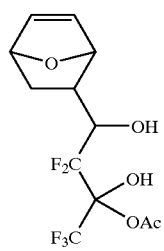
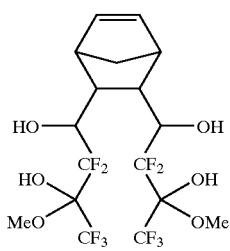
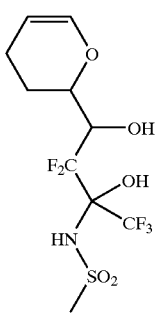
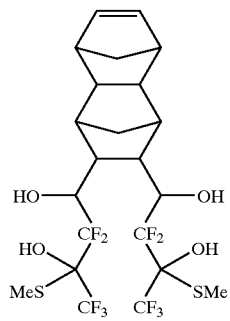
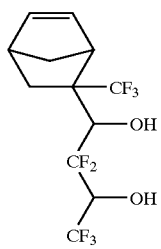
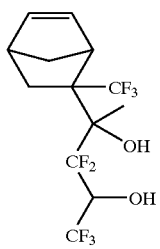
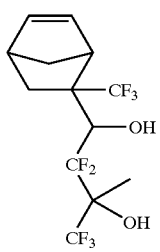

The fluorine-containing polymerizable cyclic olefin compound which has one or more partial structures represented by the above-mentioned general formula (1) desirably has a structure represented by the following general formula (3) or (4).

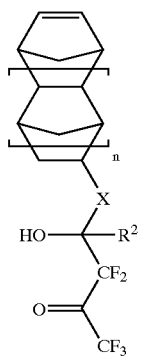

(3)

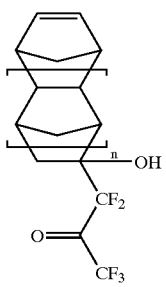

(4)

In the above-mentioned general formula (3), $R^2$ represents a hydrogen atom or a linear, branched, or cyclic alkyl group having 1–10 carbon atoms in which some or all of hydrogen atoms may be substituted with a halogen atom. Illustrative examples of $R^2$ include: a hydrogen atom, a methyl group, an ethyl group, a propyl group, an isopropyl group, a butyl group, an isobutyl group, t-butyl group, a cyclopentyl group, a cyclohexyl group, a decyl group, a trifluoro methyl group, a pentafluoro ethyl group, a heptafluoro isopropyl group. However, it is not limited to them. X represents a single bond or a linear, branched, or cyclic alkylene group having 1–10 carbon atoms in which some or all of hydrogen atoms may be substituted with a halogen atom. Illustrative examples of them include: a single bond, a methylene group, an ethylene group, 1,2-propylene group, 1,3-propylene group, 1,4-butylene group, 1,5-pentylene group, an ethylidene group, a propylidene group, an isopropylidene group, a cyclohexylidene group, a difluoro methylene group. However, it is not limited to them. n is 0 or 1.

Illustrative examples of the compound represented by the above-mentioned general formula (3) are listed below. However, it is not limited to them.

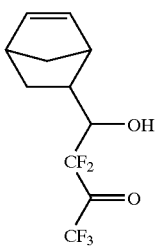
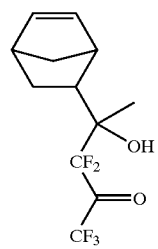
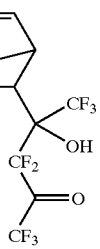

-continued

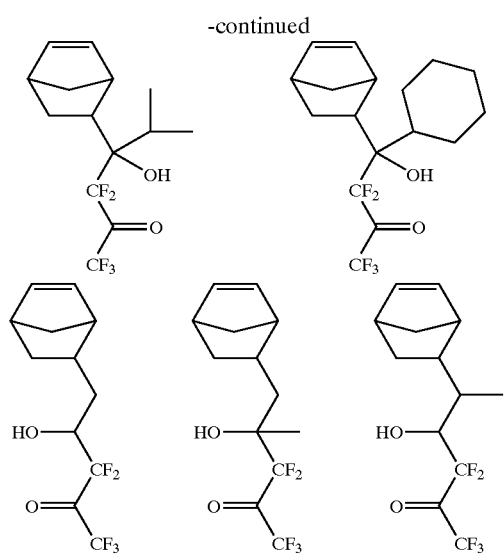

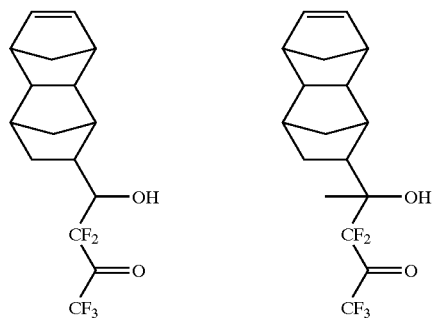

In the above-mentioned general formula (4), n is 0 or 1. The compounds represented by the above-mentioned general formula (4) are those listed below.

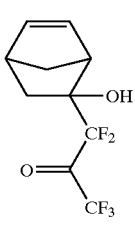 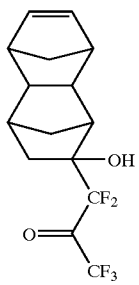

The fluorine-containing polymerizable cyclic olefin compound which has one or more partial structures represented by the above-mentioned general formula (2) desirably has the structure represented by the following general formula (5) or (6).

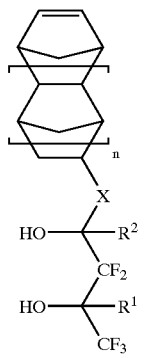

(5)

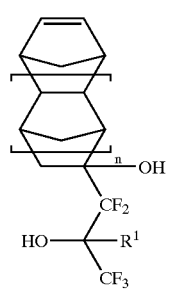

(6)

In the above-mentioned general formula (5), $R^1$, $R^2$, X and n represent those shown above. Illustrative examples of the compound represented by the above-mentioned general formula (5) are listed below. However, it is not limited to them.

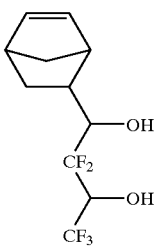 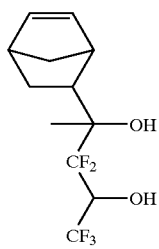

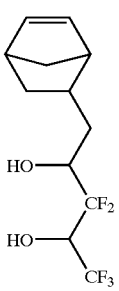 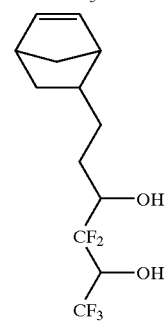

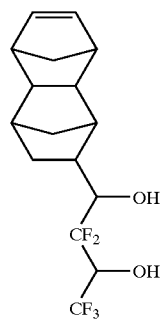 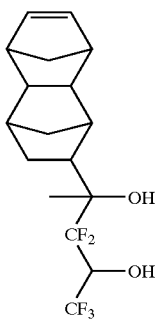 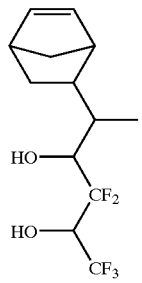 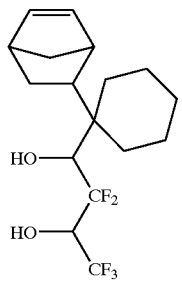
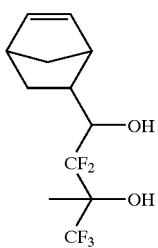 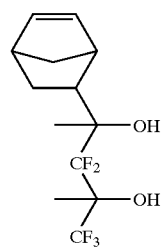 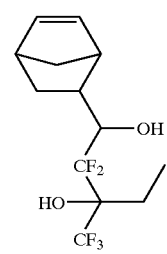 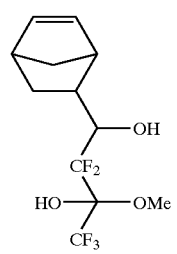
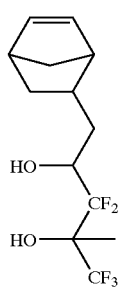 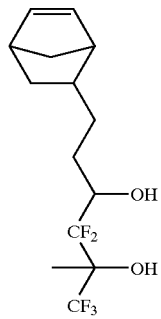 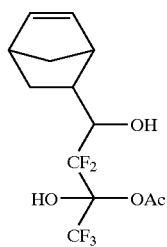 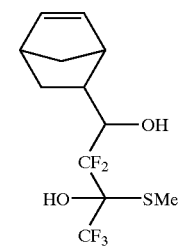
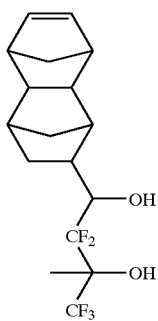 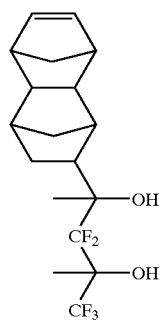 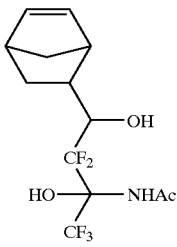 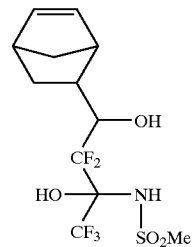
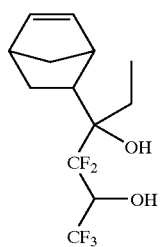 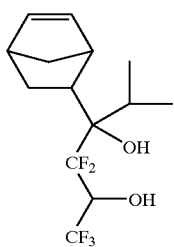 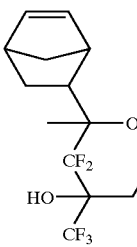 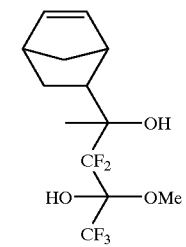
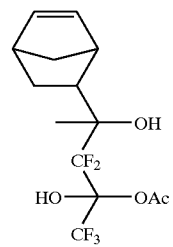 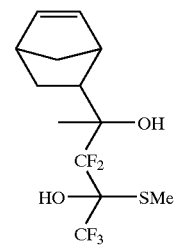

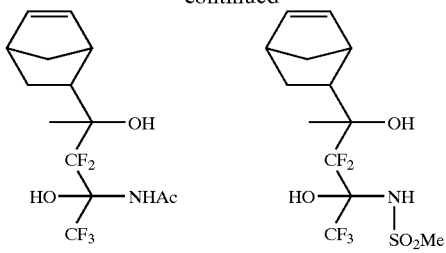

In the above-mentioned general formula (6), $R^1$ and n represent those shown above. Illustrative examples of the compound represented by the above-mentioned general formula (6) are listed below. However, it is not limited to them.

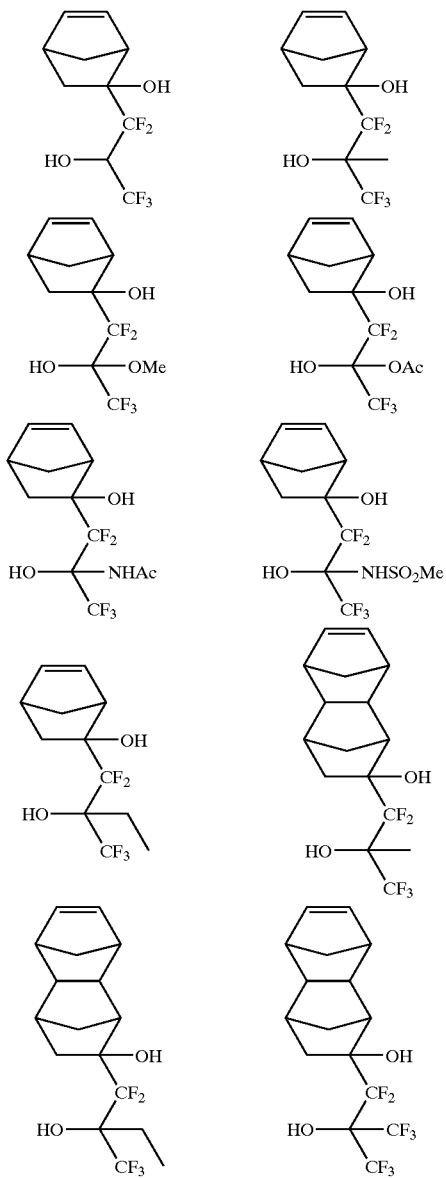

Although the compounds represented by the above-mentioned general formulae (3), (4), (5) and (6) can be preferably manufactured by the synthetic processes shown below, the present invention is not limited to these methods. Hereafter, they will be explained in detail.

The compounds represented by the above-mentioned general formulae (3) and (4) can be manufactured by the addition reaction of metal 1,1,3,3,3-pentafluoro-2-propenyloxide compound (9) to the aldehyde or ketone compound (7) or (8) respectively represented below.

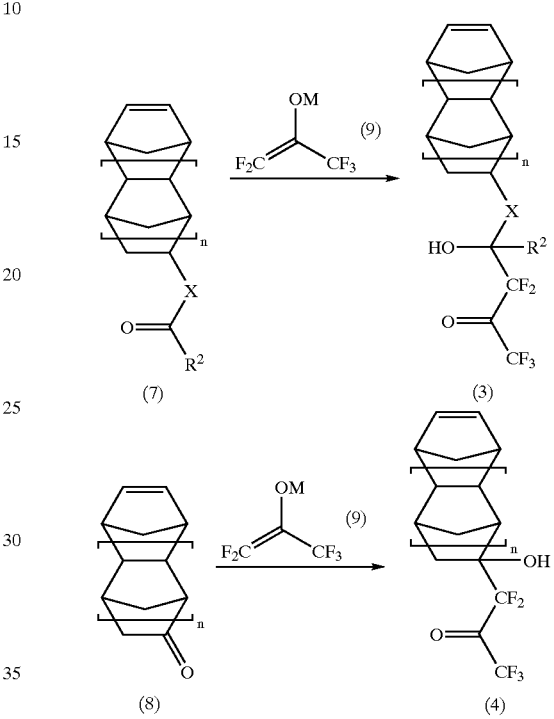

(In the formulae, $R^2$, X and n represent those shown above, M represents an alkali metal or a magnesium halide.)

This reaction is performed by mixing (9) with (7) or (8) in a solvent. Metal 1,1,3,3,3-pentafluoro-2-propenyloxide compound (9) can be prepared by a conventional method, such as Nakai et al.'s method (M=Li) (Organic Synthesis, Vol. 76, page 151, 1998), using 1,1,1,3,3,3-hexafluoro-2-propanol as a starting material. The amount of metal 1,1,3,3,3-pentafluoro-2-propenyloxide compound (9) to be used is 0.5 to 3 moles, especially 0.8 to 2 moles per mole of (7) or (8).

Examples of the solvent used herein include hydrocarbons such as toluene, hexane, and heptane; ethers such as dibutyl ether, diethylene glycol diethyl ether, diethylene glycol dimethyl ether, and tetrahydrofuran; and aprotic polar solvents such as N,N-dimethylformamide, hexamethyl phosphoric triamide, which may be used alone or in admixture.

The reaction temperature for the above-mentioned addition reaction can be suitably selected according to a structure of a starting material. In general it is preferably from −50° C. to a boiling point of the solvent, and is more preferably from −20 to 50° C. In order to improve the yield, it is desirable to determine a reaction time of the above-mentioned addition reaction by monitoring the progress of the reaction with thin-layer chromatography or gas chromatography. The reaction time is usually about 0.1–50 hours. After completion of the reaction, the fluorine-containing polymerizable cyclic olefin compound (3) or (4) (hydroxyl compound) as the target compound can be obtained after the standard aqueous work-up. The compounds (3) and (4) can be purified by a conventional method, such as recrystallization, chromatography, and distillation, if needed. The compound (3) or (4) may be sometimes obtained as the following four member ring hemiacetal compound (10) or (11). Alternatively, it may be obtained as the following compound (12) or (13) (a hydrate) as a result that water is added to the carbonyl carbon during work-up after reaction or purification. Furthermore, depending on the case, it may be obtained as a mixture of two kinds, or three kinds of compounds selected from a hydroxyketone compound, a four member ring hemiacetal compound, and a hydrate. When it is obtained as a hydrate, it is possible to reproduce a compound (3) or (4) through dehydration by heat.

In addition, although the compounds (10)–(13) can be used as a monomer for manufacture of a polymer, the polymer manufactured using the compound (10)–(13) has a disadvantage that a developer solubility is unnecessarily high, and film loss of a non-exposed area is remarkably increased compared with the polymer manufactured using the monomer of the present invention, and thus it is hard to be used as a photoresist.

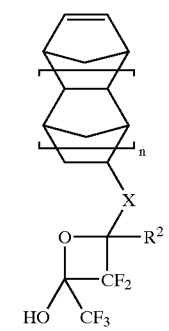

(10)

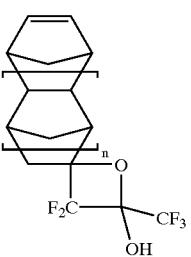

(11)

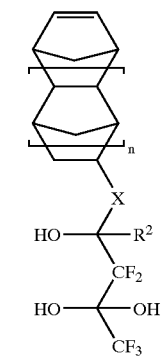

(12)

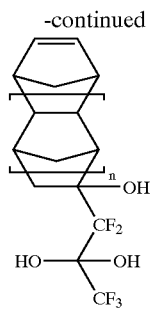

(13)

The compounds represented by the above-mentioned general formulae (5) and (6) can be manufactured by the reaction of a hydroxyketone compound (3) or (4) with $R^1$-Z which is $R^1$ anion equivalent respectively as shown below.

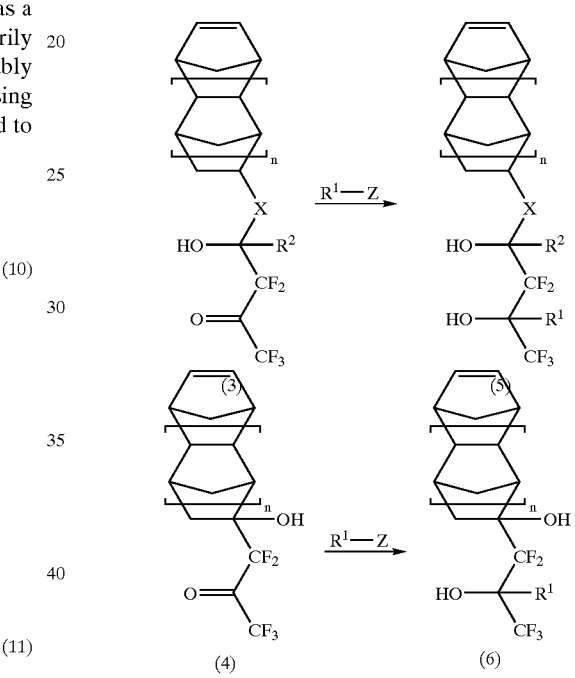

(In the formulae, $R^1$, $R^2$, X, and n represents the same as those explained above. Z represents a monovalent group wherein $R^1$-Z is $R^1$ anion equivalent.)

$R^1$-Z represents $R^1$ anion equivalent and illustrative examples of $R^1$-Z include: alcohols such as methanol and ethanol; carboxylic acids such as formic acid, acetic acid and trifluoroacetic acid; thiols such as methyl mercaptan and t-butyl mercaptan; amides such as formamide and acetamide; sulfonamides such as methanesulfonamide and trifluoromethanesulfonamide; alkyllithiums such as methyllithium and butyllithium; alkylmagnesium halides such as methylmagnesium chloride and ethylmagnesium chloride; metal hydrides, such as aluminum hydride, borane and diisobutylaluminum hydride; and metal hydride complex compounds, such as sodium borohydride and lithium aluminum hydride. However, it is not limited to them.

This reaction is performed by mixing (3) or (4) and $R^1$-Z in a solvent or without solvent. The amount of $R^1$-Z which is $R^1$ anion equivalent to be used is preferably 0.5 to 20 moles, especially 0.8 to 10 moles per mole of (3) or (4).

When reaction is performed in a solvent, a sole solvent or a mixture of two or more solvents can be used. Illustrative examples of the solvents that can be used include hydrocar bon such as toluene, hexane, and heptane; ethers such as dibutyl ether, diethylene glycol diethyl ether, diethylene glycol dimethyl ether, and tetrahydrofuran; nitrites such as acetonitrile; ketones such as acetone; esters such as ethyl acetate; and aprotic polar solvents such as N,N-dimethylformamide, hexamethyl phosphoric triamide. Although suitable reaction temperature can be selected according to the kind of $R^1$-Z to be used in the above-mentioned reaction, in general it is preferably −50° C. to the boiling point of a solvent, and is more preferably −20 to 50° C.

In order to improve the yield, it is desirable to determine a reaction time of the above-mentioned addition reaction by monitoring the progress of the reaction with thin-layer chromatography, gas chromatography, or the like. It is generally about 0.1–20 hours. After completion of the reaction, the fluorine-containing polymerizable cyclic olefin compound (5) or (6) (alcohol compound) as the desired compound can be obtained after the standard aqueous work-up. The compounds (5) and (6) can be purified by a conventional method, such as recrystallization, chromatography, and distillation, if needed.

According to the manufacturing method explained above, the fluorine-containing polymerizable cyclic olefin compound of the present invention can be manufactured easily in high yield.

Using the fluorine-containing polymerizable cyclic olefin compound of the present invention, a homopolymer or a copolymer with one or more kinds of the other polymerizable monomers can be produced by a conventional methody such as radical polymerization.

Since the polymer (a homopolymer or copolymer) that comprises as a repeating unit the fluorine-containing polymerizable cyclic olefin compound of the present invention is excellent in transparency to the irradiation at a wavelength of 200 nm or less, especially at a wavelength of 160 nm or less, and in dry etching resistance, and has a good development characteristics since it has an adequate hydrophilic property, and it is used suitably as a base resin especially for a photoresist composition. Examples of the above-mentioned irradiation at a wavelength of 160 nm or less include: $F_2$ laser light (157 nm), $Ar_2$ laser light (126 nm), extreme ultraviolet radiation (EUV:13 nm).

EXAMPLES

The present invention will be specifically explained with referring to examples. However, the present invention is not limited to them.

Synthetic Example 1

Synthesis of 1-(5-norbornene-2-yl)-2,2,4,4,4-pentafluorobutane-1,3,3-triol (The Following Structural Formula)

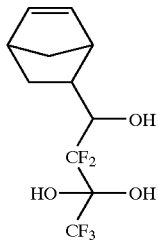

1290 mL of butyllithium (1.6 M hexane solution) was added to a mixture of 168 g of 1,1,1,3,3,3-hexafluoro-2-propanol and 1200 g of tetrahydrofuran at −70° C. under a nitrogen atmosphere. The temperature was increased to 0° C. gradually, and stirred at the temperature for 30 minutes. Then, 134 g of 5-norbornene-2-carbaldehyde was added thereto at 0° C. After stirring for 1 hour, dilute hydrochloric acid was added to terminate the reaction and to neutralize it. After the standard aqueous work-up, the product was purified by silica gel column chromatography to yield 230 g of 1-(5-norbornene-2-yl)-2,2,4,4,4-pentafluorobutane-1,3,3-triol (yield from 1,1,1,3,3,3-hexafluoro-2-propanol was 80%)

In this reaction, ketone was hydrated with acid treatment after the reaction, and the product was obtained as a hydrate.

Identification of this compound was performed by IR and NMR analysis. The analysis result is shown below.

(IR, NMR Analysis Result)

IR: (KBr)

ν=3409, 3288, 3062, 2979, 2946, 2923, 2879, 1486, 1454, 1423, 1338, 1311, 1255, 1241, 1207, 1172, 1153, 1112, 1076, 1025, 900, 842, and 711 cm$^{-1}$ $^1$H-NMR (300 MHz in DMSO-δ 6) Spectrum of main isomers: δ=0.72 (1H, m), 1.18 (1H, br.d, J=8.0 Hz), 1.29 (1H, br.d, J=8.0 Hz), 1.74 (1H, ddd, J=12.0, 9.0, 3.7 Hz), 2.44 (1H, m), 2.77 (1H, m), 3.02 (1H, m), 3.52 (1H, ddd, J=22.0, 10.6, 7.4 Hz), 6.02 (1H, dd, J=5.7, 2.8 Hz), 6.19 (1H, dd, J=5.7, 3.0 Hz), 6.29 (1H, d, J=7.4 Hz), 7.37 (1H, s), 7.96(1H, d, J=1.9 Hz).

$^{19}$F-NMR (283 MHz in CDCl$_3$) Spectrum of main isomers: δ=−130.0 (1F), −120.6 (1F), −82.0 (3F)

Example 1

Synthesis of 1-hydroxy-1-(5-norbornene-2-yl)-2,2,4,4-pentafluorobutane-3-one (The Following Structural Formula)

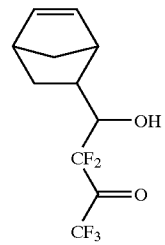

A mixture of 288 g of 1-(5-norbornene-2-yl)-2,2,4,4,4-pentafluorobutane-1,3,3-triol (synthesized according to [Synthetic example 1]) and 1500 g of toluene was heated under reflux for 2 hours, removing the water produced. After cooling, toluene was removed by evaporation under reduced pressure, and 270 g of 1-hydroxy-1-(5-norbornene-2-yl)-2,2,4,4,4-pentafluorobutane-3-one was obtained (quantitative yield).

Identification of this compound was performed by IR and NMR analysis. The analysis result is shown below.

(IR, NMR Analysis Result)

IR (thin film)

ν=1785 cm$^{-1}$ (C=O)

$^{13}$C-NMR (75 MHz in DMSO-δ 6) Spectrum of main isomers:

δ=182.3 (carbonyl carbon).

Example 2

Synthesis of 1-(5-norbornene-2-yl)-2,2,4,4,4-pentafluorobutane-1,3-diol (The Following Structural Formula)

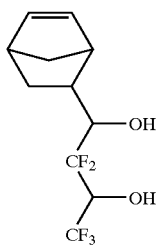

210 mL of diisobutylaluminum hydride (1.0M toluene solution) was added under nitrogen atmosphere at 0° C. to the mixture of 27.0 g of 1-hydroxy-1-(5-norbornene-2-yl)-2,2,4,4,4-pentafluorobutane-3-one (synthesized according to [Example 1]) and 50 g of toluene, then the solution was stirred for 10 hours at 20° C. Dilute hydrochloric acid was added to quench the reaction and to neutralize it, and then the standard aqueous work-up was performed. The product was purified by silica gel column chromatography to yield 25.9 g of 1-(5-norbornene-2-yl)-2,2,4,4,4-pentafluorobutane-1,3-diol (yield was 95%).

Identification of this compound was performed by IR and NMR analysis. The analysis result is shown below.

(IR, NMR Analysis Result)

IR: (KBr)

ν=3421, 3068, 2977, 2877, 1454, 1378, 1338, 1278, 1209, 1184, 1168, 1147, 1011, 1076, 1041, 1031, 1020, 846, 831, and 721 cm$^{-1}$ $^1$H-NMR (300 MHz in DMSO-δ 6) Spectrum of main isomers: δ=0.75 (1H, m), 1.10–1.35 (2H, m), 1.75 (1H, m), 2.41 (1H, m), 2.77 (1H, m), 2.85–3.30 (2H, m), 4.50 (1H, m), 5.45–5.90 (1H, m), 5.99 (1H, m), 6.18 (1H, m), and 7.12 (1H, m).

$^{19}$F-NMR (283 MHz in DMSO-δ 6) spectrum of main isomers:

δ=−120.8 (1F), −116.4 (1F), −73.5(3F).

Example 3

Synthesis of 3-methoxy-1-(5-norbornene-2-yl)-2,2,4,4,4-pentafluorobutane-1,3-diol (The Following Structural Formula)

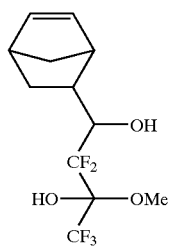

3.2 g of methanol was added under nitrogen atmosphere at 20° C. to the mixture of 27.0 g of 1-hydroxy-1-(5-norbornene-2-yl)-2,2,4,4,4-pentafluorobutane-3-one (synthesized according to [Example 1]) and 100 g of tetrahydrofuran, and stirred for 10 hours. The tetrahydrofuran was evaporated under reduced pressure, to yield 302 g of 3-methoxy-1-(5-norbornene-2-yl)-2,2,4,4,4-pentafluorobutane-1,3-diol (quantitative yield).

Identification of this compound was performed by IR and NMR analysis.

Example 4

Synthesis of 3-methylthio-1-(5-norbornene-2-yl)-2,2,4,4,4-pentafluorobutane-1,3-diol (The following Structural Formula)

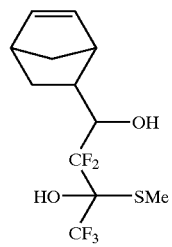

3-methylthio-1-(5-norbornene-2-yl)-2,2,4,4,4-pentafluorobutane-1,3-diol was obtained by the same method as [Example 3] except that the equivalent moles of methyl mercaptan was used instead of methanol (quantitative yield).

Identification of this compound was performed by IR and NMR analysis.

Example 5

Synthesis of 3-(acetoamino)-1-(5-norbornene-2-yl)-2,2,4,4,4-pentafluorobutane-1,3-diol (The Following Structural Formula)

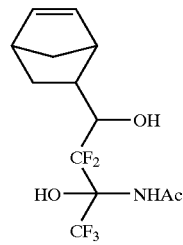

3-(acetoamino)-1-(5-norbornene-2-yl)-2,2,4,4,4-pentafluorobutane-1,3-diol was obtained by the same method as [Example 3] except that the equivalent moles of acetamide was used instead of methanol (quantitative yield).

Identification of this compound was performed by IR and NMR analysis.

Example 6

Synthesis of 3-(methanesulfonylamino)-1-(5-norbornene-2-yl)-2,2,4,4,4-pentafluorobutane-1,3-diol (The Following Structural Formula)

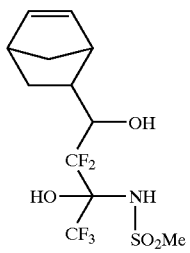

3-(methanesulfonylamino)-1-(5-norbornene-2-yl)-2,2,4,4,4-pentafluorobutane-1,3-diol was obtained by the same method as [Example 3] except that the equivalent moles of methanesulfonamide was used instead of methanol (quantitative yield).

Identification of this compound was performed by IR and NMR analysis.

Example 7

Synthesis of 3-methyl-1-(5-norbornene-2-yl)-2,2,4,4,4-pentafluorobutane-1,3-diol (The Following Structural Formula)

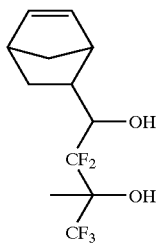

3-methyl-1-(5-norbornene-2-yl)-2,2,4,4,4-pentafluorobutane-1,3-diol was obtained by the same method as [Example 3] except that the equivalent moles of methylmagnesium chloride (tetrahydrofuran solution) was used instead of methanol, and aqueous work-up and chromatography purification were performed after the completion of the reaction (yield was 91%).

Identification of this compound was performed by IR and NMR analysis.

Synthetic Example 2

Synthesis of 4-(5-norbornene-2-yl)-1,1,1,3,3-pentafluoropentane-2,2,4-triol (The Following Structural Formula)

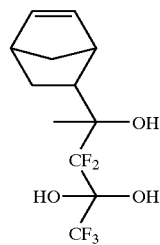

4-(5-norbornene-2-yl)-1,1,1,3,3-pentafluoropentane-2,2,4-triol was obtained by the same method as [Synthetic example 1] except that the equivalent moles of methyl (5-norbornene-2-yl) ketone was used instead of 5-norbornene-2-carbaldehyde and the reaction was conducted at 20° C. for 10 hours (65% yields)

Identification of this compound was performed by IR and NMR analysis.

Example 8

Synthesis of 4-(5-norbornene-2-yl)-1,1,1,3,3-pentafluoropentane-2,4-diol (The Following Structural Formula)

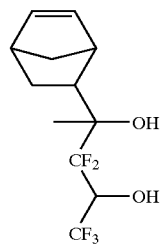

4-(5-norbornene-2-yl)-1,1,1,3,3-pentafluoropentane-2,4-diol was obtained by the same method as [Example 1], [Example 2] except that the equivalent moles of 4-(5-norbornene-2-yl)-1,1,1,3,3-pentafluoropentane-2,2,4-triol (synthesized according to [Synthetic example 2]) was used instead of 1-(5-norbornene-2-yl)-2,2,4,4,4-pentafluorobutane-1,3,3-triol (yield was 93%).

Identification of this compound was performed by IR and NMR analysis.

Synthetic Example 3

Synthesis of 2-(2,2-dihydroxy-1,1,3,3,3-pentafluoropropyl)-5-norbornene-2-ol (The Following Structural Formula)

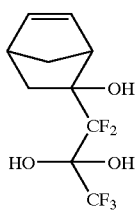

2-(2,2-dihydroxy-1,1,3,3,3-pentafluoropropyl)-5-norbornene-2-ol was obtained by the same method as [Synthetic example 1] except that the equivalent moles of 5-norbornene-2-on was used instead of 5-norbornene-2-carbaldehyde, and that the reaction was performed at 20° C. for 10 hours (yield was 58%).

Identification of this compound was performed by IR and NMR analysis.

Example 9

Synthesis of 2-(2-hydroxy-1,1,3,3,3-pentafluoropropyl)-5-norbornene-2-ol (The Following Structural Formula)

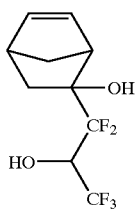

2-(2-hydroxy-1,1,3,3,3-pentafluoropropyl)-5-norbornene-2-ol was obtained by the same method as [Example 1], [Example 2] except that the equivalent moles of 2-(2,2-dihydroxy-1,1,3,3,3-pentafluoropropyl)-5-norbornene-2-ol (synthesized according to [Synthetic example 3]) was used instead of 1-(5-norbornene-2-yl)-2,2,4,4,4-pentafluorobutane-1,3,3-triol (yield was 91%)

Identification of this compound was performed by IR and NMR analysis.

Synthetic Example 4

Synthesis of 1-(8-tetracyclo[4.4.0.1$^{2,5}$.1$^{7,10}$] dodecene-3-yl)-2,2,4,4,4-pentafluorobutane-1,3,3-triol (The Following Structural Formula)

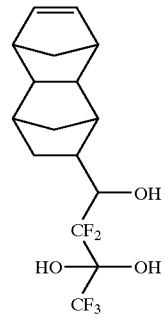

1-(8-tetracyclo[4.4.0.1$^{2,5}$.1$^{7,10}$] dodecene-3-yl)-2,2,4,4,4-pentafluorobutane-1,3,3-triol was obtained by the same method as [Synthetic example 1] except that the equivalent moles of 8-tetracyclo[4.4.0.1$^{2,5}$.1$^{7,10}$]dodecene-3-carbaldehyde was used instead of 5-norbornene-2-carbaldehyde. (yield was 77%)

Identification of this compound was performed by IR and NMR analysis.

Example 10

Synthesis of 1-(8-tetracyclo[4.4.0.1$^{2,5}$.1$^{7,10}$] dodecene-3-yl)-2,2,4,4,4-pentafluorobutane-1,3-diol (The Following Structural Formula)

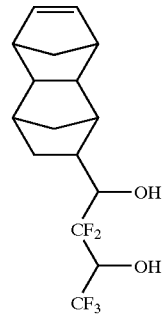

1-(8-tetracyclo[4.4.0.1$^{2,5}$.1$^{7,10}$]dodecene-3-yl)-2,2,4,4,4-pentafluorobutane-1,3-diol was obtained by the same method as [Example 1], [Example 2] except that the equivalent moles of 1-(8-tetracyclo[4.4.0.1$^{2,5}$.1$^{7,10}$]dodecene-3-yl)-2,2,4,4,4-pentafluorobutane-1,3,3-triol (synthesized according to [Synthetic example 4]) was used instead of 1-(5-norbornene-2-yl)-2,2,4,4,4-pentafluorobutane-1,3,3-triol (yield was 90%).

Identification of this compound was performed by IR and NMR analysis.

The results of the above-mentioned Examples 1–10 show that the fluorine-containing polymerizable cyclic olefin compound of the present invention can be easily manufactured in high yield.

Example 11

(Synthesis of a Polymer)

7.32 g of 1-(5-norbornene-2-yl)-2,2,4,4,4-pentafluorobutane-1,3-diol (synthesized according to [Example 2]) and 12.68 g of tert-butyl α-trifluoromethylacrylate were placed in a 200 mL flask, and dissolved in 3.53 g of ethyl acetate, and oxygen in a system was fully removed. Then, 0.33 g of AIBN (2,2'-azobis isobutyronitril) as an initiator was placed therein, and the temperature is elevated to 65° C., and the polymerization was carried out for 24 hours.

In order to purify the obtained polymer, the resulting mixture was poured into hexane, and the obtained polymer was precipitated. Furthermore, the operation wherein the obtained polymer was dissolved in THF (tetrahydrofuran) and precipitated by pouring it into 2 L of hexane was repeated twice, and then the polymer was separated and dried.

It was confirmed that 11.9 g of the white polymer thus obtained has a weight average molecular weight of 8,200 as measured by a light scattering measurement, and a dispersion (=Mw/Mn) obtained from the GPC elution diagram of 1.5. It was confirmed from the measurement result of $^1$H-NMR that the content ratio (molar ratio) of 1-(5-norbornene-2-yl)-2,2,4,4,4-pentafluorobutane-1,3-diol, and tert-butyl α-trifluoromethylacrylate in the obtained polymer was 40:60.

(Determination of Transmittance of a Polymer)

1 g of the obtained polymer was fully dissolved in 20 g of propylene glycol monomethyl ether acetate (hereinafter abbreviated as PGMEA), and filtrated through a 0.2 μm filter, to prepare the polymer solution.

After applying the solution of this polymer by spin coating onto a $MgF_2$ substrate, it was baked at 100° C. for 90 seconds using a hot plate to give a 100 nm thick polymer film on the $MgF_2$ substrate. This substrate was installed in the vacuum-ultraviolet photometer (VUV-200 S, manufactured by Nihon Bunkou), and a transmittance at a wavelength of 248 nm, 193 nm, and 157 nm was determined. Consequently, transmittance was 99% at a wavelength of 248 nm, 94% at a wavelength of 193 nm, and 52% at a wavelength of 157 nm. Therefore, it has been found that high transparency can be achieved at a wavelength of 200 nm or less, especially at a wavelength of 160 nm or less.

(Preparation of Photoresist Composition and Exposure)

The solution of photoresist composition was prepared by a conventional method using the obtained polymer. Next, on a silicon wafer on which a film of DUV-30 (manufactured by Brewer Science) was formed at a thickness of 85 nm, the prepared solution of the photoresist composition was spin coated and then baked for 90 seconds at 100° C. using a hot plate to give a photoresist film 200 nm thick. It was exposed by $F_2$ laser (VUVES, manufactured by Litho Tech) changing the exposure dose, and was baked for 90 seconds at 120° C. immediately after exposure. Development was performed for 60 seconds in the aqueous solution of 2.38% of tetramethylammonium hydroxide, and the relation between the exposure dose and a remaining rate of the film was determined. The sensitivity of the resist was determined as Eth, which is the exposure dose when a film thickness becomes 0. And tan θ of the inclination at Eth was determined as γ. From the result of VUVES exposure, it was revealed that a thickness was decreased with increase of the exposure dose, and it shows characteristics of a positive type resist. Moreover, it was exposed using the KrF scanner (S203B, manufactured by Nikon, NA 0.68, σ0.75, ⅔ annular illumination, Cr mask), and the minimum pattern size which could be resolved at the exposure dose when 150 nm line and space pattern was resolved in 1:1, was determined as a limiting resolution.

Consequently, Eth was 7 mJ/cm, γ was 13 and a limiting resolution was 125 nm, and it was revealed that its development characteristics were very excellent.

(Dry Etch Resistance Examination)

After dissolving 2 g of the obtained polymer in 10 g of PGMEA and filtered through a 0.2 μm filter. The polymer solution was spin coated to form a film 300 nm thick on a silicon substrate. Then, etch resistance was evaluated using two types of gas, $CHF_3/CF_4$ gas and $Cl_2/BCl_3$ gas.

Consequently, it was revealed that the etching rate with $CHF_3/CF_4$ gas was 170 nm/min, and the etching rate with $Cl_2/BCl_3$ gas was 201 nm/min, and thus it also has excellent dry etching resistance.

The present invention is not limited to the above-described embodiments. The above-described embodiments are some examples, and those having the substantially same composition as that described in the appended claims and providing the similar effects are included in the scope of the present invention.

The fluorine-containing polymerizable cyclic olefin compound of the present invention can be used as a raw material for polymers, functional materials, and pharmaceutical and agricultural chemicals.

What is claimed is:

1. A fluorine-containing polymerizable cyclic olefin compound that has one or more partial structures represented by the following general formula (1) or (2),

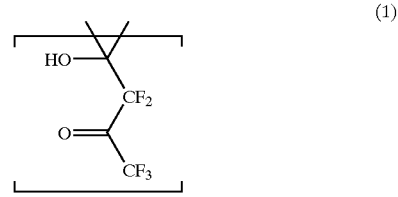

(1)

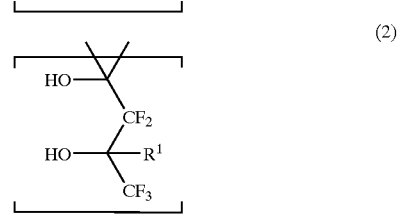

(2)

, wherein the compound is a fluorine-containing polymerizable cyclic olefin compound and $R^1$ represents a hydrogen atom, or any one of a linear, branched or cyclic alkyl group, alkoxy group, acyloxy group, alkylthio group, acyl amino group, and alkyl sulfonyl amino group having 1–15 carbon atoms in which some or all of hydrogen atoms may be substituted with a halogen atom.

2. The fluorine-containing polymerizable cyclic olefin compound according to claim 1 that is represented by any one of the following general formulae (3), (4), (5) and (6),

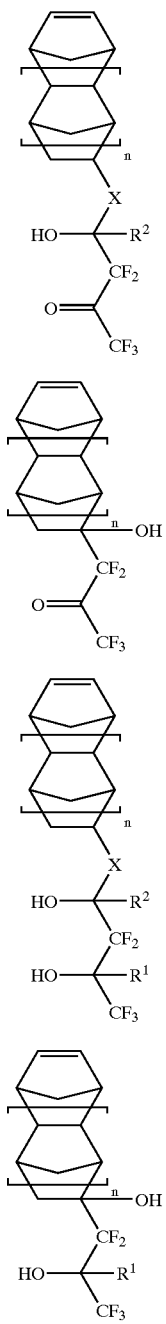

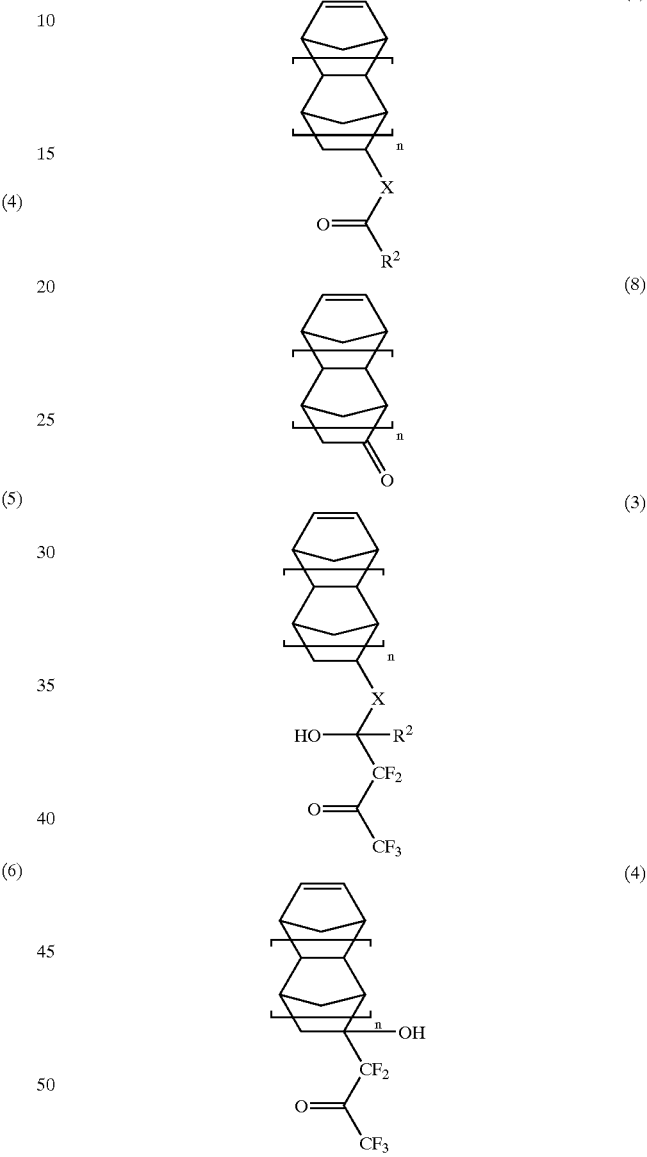

3. A manufacturing method of a fluorine-containing polymerizable cyclic olefin compound represented by the following general formula (3) or (4) wherein a cyclic olefin compound containing an aldehyde or a ketone represented by the following general formula (7) or (8) is reacted with metal 1,1,3,3,3-pentafluoro-2-propenyloxide compound, wherein $R^1$ represents a hydrogen atom or any one of a linear, branched, or cyclic alkyl group, alkoxy group, acyloxy group, alkylthio group, acyl amino group or alkyl sulfonyl amino group having 1–15 carbon atoms in which some or all of hydrogen atoms may be substituted with a halogen atom, $R^2$ represents a hydrogen atom or a linear, branched, or cyclic alkyl group having 1–10 carbon atoms in which some or all of hydrogen atoms may be substituted with a halogen atom, X represents a single bond or a linear, branched, or cyclic alkylene group having 1–10 carbon atoms in which some or all of hydrogen atoms may be substituted with a halogen atom, and n is 0 or 1.

wherein $R^2$ represents a hydrogen atom or a linear, branched, or cyclic alkyl group having 1–10 carbon atoms in which some or all of hydrogen atoms may be substituted with a halogen atom, X represents a single bond or a linear, branched, or cyclic alkylene group having 1–10 carbon atoms in which some or all of hydrogen atoms may be substituted with a halogen atom, and n is 0 or 1.

4. A manufacturing method of a fluorine-containing polymerizable cyclic olefin compound represented by the following general formula (5) or (6) wherein a fluorine-containing polymerizable cyclic olefin compound represented by the following general formula (3) or (4) is reacted with a compound $R^1$-Z,

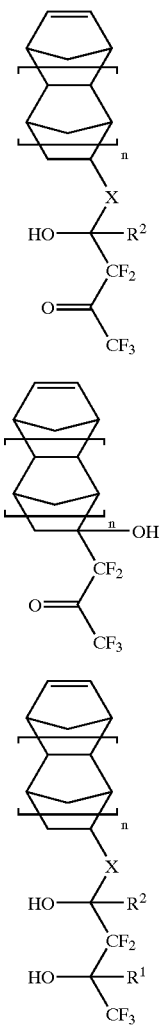

(3)

(4)

(5)

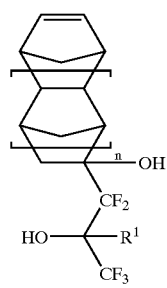

(6)

wherein $R^1$ represents a hydrogen atom, or any one of a linear, branched or cyclic alkyl group, alkoxy group, acyloxy group, alkylthio group, acyl amino group and alkyl sulfonyl amino group having 1–15 carbon atoms in which some or all of hydrogen atoms may be substituted with a halogen atom, $R^2$ represents a hydrogen atom or a linear, branched, or cyclic alkyl group having 1–10 carbon atoms in which some or all of hydrogen atoms may be substituted with a halogen atom, X represents a single bond or a linear, branched, or cyclic alkylene group having 1–10 carbon atoms in which some or all of hydrogen atoms may be substituted with a halogen atom, Z represents a monovalent group such that $R^1$-Z is $R^1$ anion equivalent and n is 0 or 1.

5. The fluorine-containing polymerizable cyclic olefin compound according to claim 1, wherein the one or more partial structures represented by the general formula (1) or (2) are attached to a cyclic structure.

* * * * *